United States Patent
Gliner et al.

(10) Patent No.: US 11,123,142 B2
(45) Date of Patent: Sep. 21, 2021

(54) QUICK REGISTRATION OF COORDINATE SYSTEMS FOR ROBOTIC SURGERY

(71) Applicant: Biosense Webster (Israel) Ltd., Yokneam (IL)

(72) Inventors: Vadim Gliner, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 139 days.

(21) Appl. No.: 16/211,594

(22) Filed: Dec. 6, 2018

(65) Prior Publication Data
US 2020/0179064 A1 Jun. 11, 2020

(51) Int. Cl.
*A61B 34/20* (2016.01)
*B25J 9/16* (2006.01)
*G01B 7/004* (2006.01)
*A61B 34/30* (2016.01)

(52) U.S. Cl.
CPC ............ *A61B 34/20* (2016.02); *B25J 9/1692* (2013.01); *G01B 7/004* (2013.01); *A61B 2034/301* (2016.02)

(58) Field of Classification Search
CPC ......... A61B 5/062; A61B 34/20; A61B 34/30; A61B 34/32; A61B 34/35; A61B 34/37; A61B 34/70; A61B 2034/2051; A61B 2034/2055; A61B 2034/2059; A61B 2034/301; B25J 9/1692
See application file for complete search history.

(56) References Cited

U.S. PATENT DOCUMENTS

| | | | |
|---|---|---|---|
| 7,809,421 | B1 | 10/2010 | Govari |
| 2002/0049375 | A1 | 4/2002 | Strommer et al. |
| 2006/0095022 | A1 | 5/2006 | Moll et al. |
| 2009/0030307 | A1 | 1/2009 | Govari et al. |
| 2009/0264727 | A1 | 10/2009 | Markowitz et al. |
| 2014/0330114 | A1 | 11/2014 | Navab |

(Continued)

OTHER PUBLICATIONS

Reichl, et al., "Electromagnetic Servoing—A New Tracking Paradigm," Aug. 2013, IEEE Transactions on Medical Imaging, vol. 32, No. 8, pp. 1526-1535 (Year: 2013).*

(Continued)

*Primary Examiner* — Spencer D Patton
(74) *Attorney, Agent, or Firm* — Todd J. Burns (57) ABSTRACT

A method for controlling a robot, which moves an ensemble that includes an arm and a tool, includes receiving from the robot, at one or more times, an arm-tracking signal, which indicates an arm-pose of the arm relative to a robot coordinate system (RCS) of the robot, deriving, from the arm-tracking signal, respective RCS-poses of at least one portion of the ensemble, relative to the RCS, at the times, receiving, from a tracking system, a sensor-tracking signal, which indicates a sensor-pose of at least one sensor, which belongs to the tracking system and is coupled to the ensemble, relative to a tracking-system coordinate system (TCS) of the tracking system, deriving, from the sensor-tracking signal, respective TCS-poses of the portion of the ensemble, relative to the TCS, at the times, registering the RCS to the TCS based on the RCS-poses and the TCS-poses, and, based on the registering, controlling the robot.

48 Claims, 3 Drawing Sheets

(56) References Cited

U.S. PATENT DOCUMENTS

| | | |
|---|---|---|
| 2015/0119637 A1 | 4/2015 | Alvarez et al. |
| 2017/0151027 A1 | 6/2017 | Walker et al. |
| 2017/0231702 A1 | 8/2017 | Crawford et al. |
| 2017/0290631 A1 | 10/2017 | Lee et al. |
| 2018/0256259 A1* | 9/2018 | Crawford ............. A61B 6/5217 |

OTHER PUBLICATIONS

European Search Report dated May 6, 2020 from corresponding European Patent Application No. 19213798.2.

Reichl, Tobias et al., "Electromagnetic Servoing a New Tracking Paradigm", IEEE Transactions on Medical Imaging, IEEE Service Center, Piscataway, NJ, US, vol. 32, No. 8, Aug. 1, 2013, pp. 1526-1535.

Staub, Christoph et al., "Autonomous High Precision Positioning of Surgical Instruments in Robot-Assisted Minimally Invasive Surgery under Visual Guidance", Autonomic and Autonomous Systems (ICAS), 2010 Sixth International Conference on, IEEE, Piscataway, NJ, USA, Mar. 7, 2010, pp. 64-69.

Universal Robots: "UR5 Technical Specifications", Sep. 1, 2016, pp. 1-1 URL:https://www.universal-robots.com/media/50588/ur5_en.pdf.

U.S. Appl. No. 15/859,969, filed Jan. 2, 2018, Govari, et al.

https://www.youtube.com/watch?v=QGYPT1e4eAw; StealthStation ENT Video, published Jun. 1, 2017.

* cited by examiner

QUICK REGISTRATION OF COORDINATE SYSTEMS FOR ROBOTIC SURGERY

FIELD OF THE INVENTION

The present invention relates to the field of robotic surgery, including endoscopic surgery and other types of diagnostic surgery.

BACKGROUND

US Patent Application Publication 2014/0330114 describes a system for tracking a tracking element inside a body. It includes a first tracking system, which includes a first tracking sensor for detecting the current position of a tracking element inside a body relative to a nominal position with respect to the first tracking sensor, and a second tracking system, which includes a second tracking sensor for determining the position of the first tracking sensor of the first tracking system relative to the second tracking sensor, and a control unit. The first tracking sensor is movable, and the control unit is configured to deliver a correction signal indicating a deviation of the current position of the tracking element relative to a nominal position with reference to the first tracking sensor. Further, a respective tracking method is provided.

US Patent Application Publication 2015/0119637 describes an endolumenal robotic system, which provides the surgeon with the ability to drive a robotically-driven endoscopic device to a desired anatomical position. A digital camera is mounted on the endoscopic device.

US Patent Application Publication 2017/0258535 describes devices, systems, and methods for detecting a 3-dimensional position of an object, and surgical automation involving the same. The surgical robot system may include a robot having a robot base, a robot arm coupled to the robot base, and an end-effector coupled to the robot arm. The end-effector, surgical instruments, the patient, and/or other objects to be tracked include active and/or passive tracking markers. Cameras, such as stereophotogrammetric infrared cameras, are able to detect the tracking markers, and the robot determines a 3-dimensional position of the object from the tracking markers.

US Patent Application Publication 2017/0290631 describes floating electromagnetic field generator systems and methods. The system comprises a surgical bed portion. The system also comprises a brace component disposed within the surgical bed portion. Additionally, the system comprises a first arm that is attached to the brace component. The first arm is positioned adjacent to the surgical bed portion. Additionally, the first arm has at least one field generator coil embedded therein. The system also comprises a second arm that is attached to the brace component. The second arm is positioned adjacent to the surgical bed portion. Additionally, the second arm has at least one field generator coil embedded therein. The second arm is positioned parallel to the first arm.

SUMMARY OF THE INVENTION

There is provided, in accordance with some embodiments of the present invention, a system for controlling a surgical robot while the robot moves an ensemble that includes an arm of the robot and a tool that is held by the arm. The system includes a communication interface and a processor. The processor is configured to receive from the robot via the communication interface, at one or more times, an arm-tracking signal, which indicates an arm-pose of the arm relative to a robot coordinate system (RCS) of the robot. The processor is further configured to derive, from the arm-tracking signal, respective RCS-poses of at least one particular portion of the ensemble, relative to the RCS, at the one or more times. The processor is further configured to receive, from a tracking system, a sensor-tracking signal, which indicates a sensor-pose of at least one sensor, which belongs to the tracking system and is coupled to the ensemble, relative to a tracking-system coordinate system (TCS) of the tracking system. The processor is further configured to derive, from the sensor-tracking signal, respective TCS-poses of the particular portion of the ensemble, relative to the TCS, at the one or more times. The processor is further configured to, based on the RCS-poses and the TCS-poses, register the RCS and the TCS to one another, and, based on the registering, control the robot.

In some embodiments, the sensor includes a coil, and the tracking system includes a plurality of magnetic-field generators that generate a magnetic field that induces the sensor-tracking signal in the coil.

In some embodiments, the sensor is coupled to the tool.
In some embodiments, the sensor is coupled to the arm.
In some embodiments, the times are first times, the RCS-poses are first-time RCS-poses, and the TCS-poses are first-time TCS-poses, and the processor is further configured to:

receive the arm-tracking signal at a second time, derive, from the arm-tracking signal, a second-time RCS-pose of the particular portion of the ensemble, relative to the RCS, at the second time, derive, from the sensor-tracking signal, a second-time TCS-pose of the particular portion of the ensemble, relative to the TCS, at the second time, based on the registering, compute a transformed pose, by transforming the second-time TCS-pose to the RCS, compute a distance between the transformed pose and the second-time RCS-pose, and responsively to the distance being greater than a predefined threshold, reregister the RCS and the TCS to one another using the second-time RCS-pose and the second-time TCS-pose, without using the first-time RCS-poses and without using the first-time TCS-poses.

In some embodiments, the times are first times, the RCS-poses are first-time RCS-poses, and the TCS-poses are first-time TCS-poses, and the processor is further configured to:

receive the arm-tracking signal at a second time, derive, from the arm-tracking signal, a second-time RCS-pose of the particular portion of the ensemble, relative to the RCS, at the second time, derive, from the sensor-tracking signal, a second-time TCS-pose of the particular portion of the ensemble, relative to the TCS, at the second time, based on the registering, compute a transformed pose, by transforming the second-time TCS-pose to the RCS, compute a distance between the transformed pose and the second-time RCS-pose, and responsively to the distance not being greater than a predefined threshold, reregister the RCS and the TCS to one another using the second-time RCS-pose, the second-time TCS-pose, the first-time RCS-poses, and the first-time TCS-poses.

In some embodiments, the times are first times, the RCS-poses are first-time RCS-poses, and the TCS-poses are first-time TCS-poses, and the processor is further configured to:

receive the arm-tracking signal at a second time, derive, from the arm-tracking signal, a second-time RCS-pose of the particular portion of the ensemble, relative to the RCS, at the second time, derive, from the sensor-tracking signal, a second-time TCS-pose of the particular portion of the ensemble, relative to the TCS, at the second time, based on the registering, compute a transformed pose, by transforming the second-time RCS-pose to the TCS, compute a distance between the transformed pose and the second-time TCS-pose, and responsively to the distance being greater than a predefined threshold, reregister the RCS and the TCS to one another using the second-time RCS-pose and the second-time TCS-pose, without using the first-time RCS-poses and without using the first-time TCS-poses.

In some embodiments, the times are first times, the RCS-poses are first-time RCS-poses, and the TCS-poses are first-time TCS-poses, and the processor is further configured to:

receive the arm-tracking signal at a second time, derive, from the arm-tracking signal, a second-time RCS-pose of the particular portion of the ensemble, relative to the RCS, at the second time, derive, from the sensor-tracking signal, a second-time TCS-pose of the particular portion of the ensemble, relative to the TCS, at the second time, based on the registering, compute a transformed pose, by transforming the second-time RCS-pose to the TCS, compute a distance between the transformed pose and the second-time TCS-pose, and responsively to the distance not being greater than a predefined threshold, reregister the RCS and the TCS to one another using the second-time RCS-pose, the second-time TCS-pose, the first-time RCS-poses, and the first-time TCS-poses.

In some embodiments, the processor is configured to control the robot by:

computing a target arm-pose offset relative to the TCS, based on the registering, computing a transformed target arm-pose offset, by transforming the target arm-pose offset to the RCS, and causing the robot to change the arm-pose of the arm by the target arm-pose offset, by communicating the transformed target arm-pose offset to the robot.

In some embodiments, the robot is operating on a subject, the tracking system further includes at least one subject-tracking sensor coupled to the subject, and the processor is further configured to:

receive, from the tracking system, a subject-tracking signal, which indicates a subject-tracking-sensor-pose of the subject-tracking sensor relative to the TCS, and derive, from the subject-tracking signal, a change in a subject-pose of the subject, and the processor is configured to compute the target arm-pose offset in response to the change in the subject-pose of the subject.

There is further provided, in accordance with some embodiments of the present invention, a method for controlling a surgical robot while the robot moves an ensemble that includes an arm of the robot and a tool that is held by the arm. The method includes receiving from the robot, at one or more times, an arm-tracking signal, which indicates an arm-pose of the arm relative to a robot coordinate system (RCS) of the robot. The method further includes deriving, from the arm-tracking signal, respective RCS-poses of at least one particular portion of the ensemble, relative to the RCS, at the one or more times. The method further includes receiving, from a tracking system, a sensor-tracking signal, which indicates a sensor-pose of at least one sensor, which belongs to the tracking system and is coupled to the ensemble, relative to a tracking-system coordinate system (TCS) of the tracking system. The method further includes deriving, from the sensor-tracking signal, respective TCS-poses of the particular portion of the ensemble, relative to the TCS, at the one or more times. The method further includes, based on the RCS-poses and the TCS-poses, registering the RCS and the TCS to one another, and, based on the registering, controlling the robot.

The present invention will be more fully understood from the following detailed description of embodiments thereof, taken together with the drawings, in which:

DETAILED DESCRIPTION OF EMBODIMENTS

Glossary

In the context of the present application, including the claims, the "pose" of an object refers to the combination of (i) the location of the object, and (ii) the orientation of the object. Thus, for example, in a three-dimensional setting, the pose of an object may be described by a location vector (x, y, z), which describes the location of the object, together with an orientation vector (x', y', z'), which describes the orientation of the object. (Typically, the orientation vector is normalized so as to be of unit length.)

Overview

In a robotic surgical procedure, a robotic arm operates a surgical tool. For example, in a robotic otolaryngological endoscopy procedure, a robotic arm may insert an endoscope into a subject's nasal cavity or sinus, and operate the endoscope within this cavity.

In many cases, during the procedure, an icon of the tool is superimposed on a preoperative scan of the subject, such that a physician may track the movement of the tool. The physician may further specify a target pose of the tool by manipulating the icon, by manually moving the tool, or by any other suitable technique. Typically, to ensure that the tool safely attains the target pose, a tracking system tracks the pose of the tool and issues instructions to the robot in response to the tracking, such that the tool is moved incrementally toward the target pose.

In some applications, to facilitate tracking the pose of the tool, at least one tracking sensor is coupled to the arm of the robot and/or to the tool. For example, for endoscopic procedures, two or three coils may be coupled to the endoscope at predetermined positions on the endoscope, and an alternating magnetic field may be generated, at different respective frequencies, by multiple magnetic-field generators in the vicinity of the subject. Based on the various frequency components of the voltages induced in the coils, the tracking system may ascertain the respective poses of the coils, and hence, the pose of the tool.

A challenge, when performing robotic surgery as described above, is that the instructions delivered to the robot must be specified in terms of the coordinate system of the robot, which is typically different from that of the tracking system. Thus, it is typically necessary to register the coordinate system of the robot, referred to herein as the Robot Coordinate System (RCS), with that of the tracking system, referred to herein as the Tracking Coordinate System (TCS). In other words, it is necessary to find a transformation $T_{TCS \to RCS}$ that maps any pose, as specified relative to the TCS, to the RCS.

One technique for registering the two coordinate systems involves use of the Iterative Closest Point (ICP) algorithm. In particular, as the tracking sensor is moved to various different locations, two sets of coordinates of the sensor—one in the RCS and the other in the TCS—may be recorded. Subsequently, using the sets of coordinates, the ICP algorithm may be used to find $T_{TCS \to RCS}$.

Embodiments of the present invention, however, utilize an improved registration technique that offers several advantages over ICP. In particular, as the robot moves the tool, a processor ascertains not only the coordinates of the sensor, but also the orientation of the sensor. The processor thus acquires, for each pose of the sensor, a pair of corresponding vectors: (i) $p^{TCS}=(x, y, z, x', y', z')^{TCS}$, which describes the pose of the sensor relative to the TCS, and (ii) $p^{RCS}=(x, y, z, x', y', z')^{RCS}$, which describes the pose of the sensor relative to the RCS. Based on one or more such pairs of corresponding vectors, the processor computes the transformation between the two coordinate systems.

Advantageously, since each pose of the sensor includes six variables, and the registration involves only six degrees of freedom, even a single pose is sufficient for registering the two coordinate systems. Moreover, even if an iterative algorithm (such as gradient descent) is used to solve for the transformation, fewer iterations may be required, relative to ICP. Thus, the registration may be performed relatively quickly. Furthermore, there is less risk, relative to ICP, of converging to a local minimum when solving for the transformation.

Typically, as each pair of corresponding vectors is acquired, the processor applies $T_{TCS \to RCS}$ to $P^{TCS}$, thus yielding a transformed vector $P^{RCS*}$. Subsequently, the processor, using any suitable distance function, computes the distance between $P^{RCS*}$ and $P^{RCS}$. If the distance between $P^{RCS}$ and $P^{RCS*}$ is less than a predefined threshold, the processor adds the pair of corresponding vectors to the pairs that have been acquired thus far. Then, using all of the pairs, the processor computes the transformation. For example, the processor may use an optimization algorithm, such as gradient descent, to find the transformation $T_{TCS \to RCS}$ that minimizes the error function $\Sigma_{i=1}^{i=N}(P_i^{RCS} \; P_i^{RCS*})$, where D is the distance function described above.

On the other hand, if the distance is greater than the threshold, the processor assumes that the base of the robotic arm, with respect to which the coordinate system of the robot is defined, has been moved. The processor therefore discards the previously-acquired pairs of vectors, and reinitializes the transformation using the current pair, e.g., by analytically solving for $T_{TCS \to RCS}$.

Typically, the distance function that is used is a type of sum of squared errors (SSE). For example, the distance between two poses $(x_j, y_j, z_j, x'_j, y'_j, z'_j)$ and $(x_k, y_k, z_k, x'_k, y'_k, z'_k)$ may be equal to $(x_j-x_k)^2+(y_j-y_k)^2+(z_j-z_k)^2+C((x'_j-x'_k)^2+(y'_j-y'_k)^2+(z'_j-z'_k)^2)$ for a suitable constant C. Alternatively, using the orientation angles $\alpha$, $\beta$, and $\gamma$ to specify the orientation, the distance may be equal to $(x_j-x_k)^2+(y_j-y_k)^2+(z_j-z_k)^2+C((\alpha_j-\alpha_k)^2+(\beta_j-\beta_k)^2+(\gamma_j-\gamma_k)^2)$.

Immediately prior to the procedure, an additional registration, between the coordinate system of the preoperative scan and the coordinate system of the tracking system, is performed. For example, in the presence of the aforementioned magnetic field, the physician may use a shaft, which includes a coil, to touch designated portions of the subject's face. The coordinates of the tip of the shaft at these locations, as ascertained from the signal from the coil, may then be registered (e.g., using ICP) with the corresponding coordinates in the preoperative scan. In other words, the processor may compute a transformation $T_{SCS \to TCS}$, which maps any pose in the subject coordinate system (SCS) to the TCS, along with the inverse transformation $T_{TCS \to SCS}$. Thus, during the procedure, a target pose specified in the SCS may be transformed to the TCS, by applying $T_{SCS \to TCS}$ to the specified target. Conversely, the current pose of the tool may be shown on the preoperative scan, by application of $T_{TCS-SCS}$.

Typically, at least one other tracking sensor is attached to the subject (e.g., to the subject's forehead). During the procedure, the current pose of this sensor, relative to the TCS, is continually computed by the processor. If the difference between the current pose of the sensor and the most recent pose of the sensor exceeds a predefined threshold (indicating that the subject has moved), the processor recalculates $T_{SCS \to TCS}$. Alternatively or additionally, in response to the movement of the subject, the processor may recalculate the target pose for the tool relative to the TCS.

System Description

Figure 1:
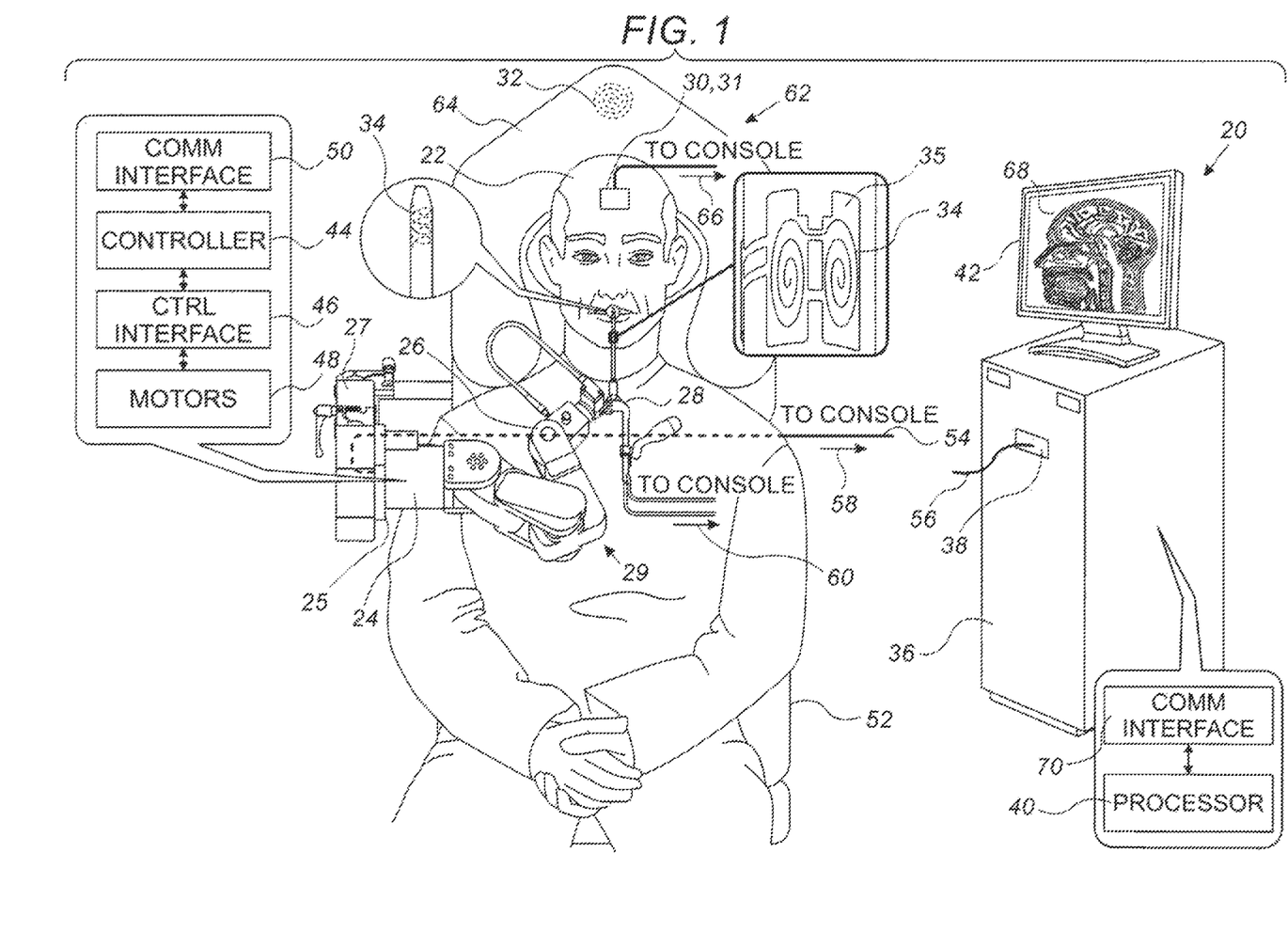
FIG. 1 is a schematic illustration of a system for performing robotic surgery on a subject, in accordance with some embodiments of the present invention.

Reference is initially made to FIG. 1, which is a schematic illustration of a system 20 for performing robotic surgery on a subject 22, in accordance with some embodiments of the present invention.

System 20 comprises a surgical robot 24, comprising an arm 26 and a controller 44. Controller 44, which is typically located within a base 25 of robot 24 that is attached to arm 26, is configured to control arm 26, typically by operating one or more motors 48 via a control (CTRL) interface 46. (Control interface 46 may comprise, for example, one or more drivers, encoders, and/or other electronic components.) In some embodiments, base 25 is connected, via a connecting arm 27, to the surgical chair 52 on which subject 22 reclines, or to the bed on which the subject lies.

Arm 26 comprises one or more interconnected segments, which are configured to move with respect to each other (e.g., by swiveling at interconnecting joints) and with respect to base 25. The distalmost segment of arm 26 is configured to hold a tool 28, such as a suction tool or an endoscope. Thus, by moving the ensemble 29 that includes arm 26 and tool 28, controller 44 may position the tool at any suitable pose within the body of subject 22. For example, controller 44 may position the distal end of an endoscope within the subject's nasal cavity or sinus, such that the endoscope may acquire images of the cavity.

System 20 further comprises a processor 40, which is typically located in a console 36. Controller 44 operates arm 26 in response to instructions received from processor 40. In addition, while arm 26 moves tool 28, controller 44 communicates an arm-tracking signal 58, which indicates the pose of the arm (in particular, of a designated point on the distalmost segment of the arm), to processor 40. For example, controller 44 may report the pose of the arm periodically, and/or in response to queries from processor 40. Arm-tracking signal 58 indicates the pose of the arm relative to the coordinate system of the robot, indicated herein by the notation "RCS," which is defined relative to the pose of base 25.

A cable 54, which runs from console 36 to robot 24, comprises electrical wiring that carries power to the robot. Controller 44 exchanges communication with processor 40 via a communication (COMM) interface 50, which may comprise any suitable circuitry and/or other hardware. In some embodiments, communication interface 50 is a wired communication interface; in such embodiments, cable 54 may comprise wiring that carries communication signals between the controller and the processor. In other embodiments, the communication interface is a wireless communication interface.

Cable 54 is connected to console 36 via a first electrical interface 38 (comprising, for example, a port or socket), and to robot 24 via a second electrical interface. In some embodiments, the console-facing end of cable 54 is bundled, together with the respective ends of the various other cables described herein, in a central cable 56.

System 20 further comprises a tracking system 62, comprising at least one tool-tracking sensor that is coupled to ensemble 29 (i.e., either to tool 28 or to arm 26). While the robot moves the ensemble (together with the tool-tracking sensor), tracking system 62 outputs a sensor-tracking signal 60 to processor 40. Sensor-tracking signal 60 indicates the pose of the tool-tracking sensor relative to the coordinate system of the tracking system, indicated herein by the notation "TCS."

In some embodiments, tracking system 62 comprises an electromagnetic tracking system, in that sensor-tracking signal 60 includes one or more electromagnetically-induced voltages that indicate the pose of the tool. For example, as shown in FIG. 1, tracking system 62 may comprise one or more (typically, two or three) electromagnetic tool-tracking sensors, comprising respective ensemble-coupled coils 34 that are coupled to ensemble 29. Tracking system 62 may further comprise a plurality of (e.g., between 10 and 20) stationary coils 32, which are disposed at different respective positions in the vicinity of subject 22, e.g., within a support 64 positioned at the head of chair 52. (For simplicity, only one stationary coil 32 is shown in FIG. 1.) Alternating currents are passed through stationary coils 32 (or through subsets of the stationary coils) at different respective frequencies, such that the stationary coils generate a magnetic field that induces respective voltages, at the different frequencies, in ensemble-coupled coils 34. The induced voltages indicate the respective pose of each ensemble-coupled coil, and hence, the pose of the tool.

Alternatively, ensemble-coupled coils 34 may generate a magnetic field that induces respective voltages in stationary coils 32. (In such embodiments, sensor-tracking signal 60 is output by stationary coils 32, rather than by ensemble-coupled coils 34.) As in the previously-described embodiment, the induced voltages indicate the respective pose of each ensemble-coupled coil.

Ensemble-coupled coils 34 may be coupled to arm 26 or to tool 28 in any suitable manner. For example, as shown in FIG. 1, at least one coil 34 may comprise a looped trace formed on the surface of a flexible circuit 35 that is coupled to the tool. Alternatively or additionally, as further shown in FIG. 1, at least one coil may be disposed within tool 28. As yet another alternative, at least one coil may be coiled around arm 26 or tool 28, e.g., within grooves that are formed on the surface of arm 26 or tool 28.

Alternatively or additionally to an electromagnetic system, tracking system 62 may comprise an optical tracking system, comprising an optical marker that is coupled to ensemble 29, and one or more cameras. In such embodiments, sensor-tracking signal 60 includes images, output by the cameras, which indicate the pose of the optical marker relative to the cameras.

Typically, tracking system 62 further comprises a subject-tracking sensor 30, which is coupled to subject 22, e.g., to the subject's forehead. (Sensor 30 is typically contained within an adhesive patch 31.) Tracking system 62 outputs a subject-sensor-tracking signal 66, which indicates the pose of sensor 30 relative to the TCS. Sensor 30 may comprise, for example, one or more receiving or generating coils, as described above for the tool-tracking sensor. Alternatively or additionally, an optical marker, for use in an optical tracking system, may be coupled to subject 22.

In addition to processor 40 and electrical interface 38, console typically comprises a wired or wireless communication (COMM) interface 70 for communicating with robot 24, and a monitor 42, configured to display a preoperative scan 68 of the subject. Using monitor 42, a physician may visually track the movement of tool 28 during the procedure, and/or specify a target pose for the tool, e.g., by drawing or moving an icon superimposed over preoperative scan 68. Respective cables connect ensemble-coupled coils 34, stationary coils 32, subject-tracking sensor 30, and tool 28 to console 36.

In general, processor 40 may be embodied as a single processor, or as a cooperatively networked or clustered set of processors. In some embodiments, the functionality of processor 40, as described herein, is implemented solely in hardware, e.g., using one or more Application-Specific Integrated Circuits (ASICs) or Field-Programmable Gate Arrays (FPGAs). In other embodiments, the functionality of processor 40 is implemented at least partly in software. For example, in some embodiments, processor 40 is embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Registering the TCS and RCS to One Another

While the robot moves ensemble 29, processor 40 repeatedly registers the TCS and the RCS to one another. This registration is based on one or more pairs of corresponding poses of at least one particular portion of ensemble 29. For example, the registration may be based on one or more pairs of corresponding poses for each portion of the ensemble to which one of coils 34 is coupled, and/or for the distal end of tool 28. Each $i^{th}$ pair of corresponding poses includes (i) the pose $P_i^{TCS}$ of the particular portion of the ensemble relative to the TCS at a time $t_i$, and (ii) the pose $P_i^{RCS}$ of the particular portion of the ensemble relative to the RCS at time $t_i$.

(It is noted that $P_i^{TCS}$ and $P_i^{RCS}$ are said to "correspond" to one another by virtue of describing the same objective pose, i.e., the pose of the particular portion of the ensemble at time $t_i$. Since the robotic arm typically moves relatively slowly, $P_i^{TCS}$ and $P_i^{RCS}$ may be said to correspond to one another even if several milliseconds (e.g., 0-5 or 5-10 milliseconds) separate the respective times of the two poses. In other words, "time $t_i$" may actually include an interval of several milliseconds.)

Although even a single pair of corresponding poses is sufficient for registering the two coordinate systems to one another, the accuracy of the registration generally increases with the number of pairs used for the registration. Hence, the processor typically accumulates pairs of corresponding poses and repeatedly registers the two coordinate systems based on all of the pairs that have been accumulated thus far, provided that base 25 did not move during the acquisition of the pairs.

In other words, the processor maintains a set $\{(P_i^{TCS}, P_i^{RCS})\}$ of pairs of corresponding poses for each relevant portion of the ensemble. As the procedure is performed, the processor continually adds new pairs of poses to the set and reregisters the two coordinate systems to one another, until the processor ascertains that the base of the robot was moved. In response to ascertaining that the base was moved, the processor empties the set, and then reinitializes the set with the most recent pair of corresponding poses.

More specifically, at each time $t_i$, the processor receives the arm-tracking signal from the robot and, based on the arm-tracking signal, computes the RCS-pose (i.e., the pose relative to the RCS) of the particular portion of the ensemble. The processor further receives sensor-tracking signal 60 from the tracking system, and, based on the sensor-tracking signal, computes the respective TCS-poses of the particular portion of the ensemble at times $\{t_i\}$. (Typically, the processor continuously receives sensor-tracking signal 60 as the procedure is performed.) Based on the RCS-poses and the TCS-poses, the processor registers the RCS and the TCS to one another.

Figure 2:
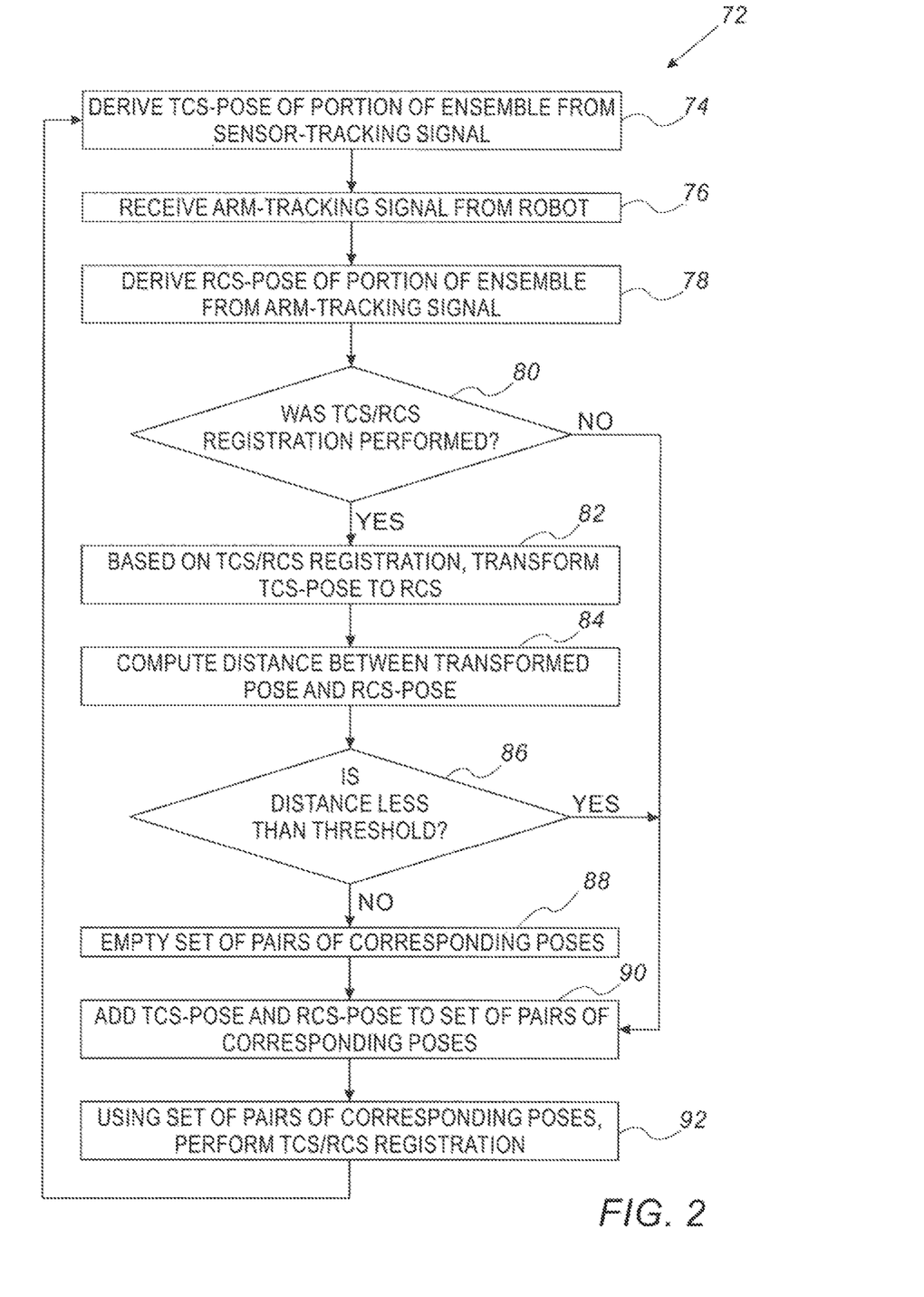
FIG. 2 is a flow diagram for a method and algorithm for registering two coordinate systems to one another, in accordance with some embodiments of the present invention.

In this regard, reference is now made to FIG. 2, which is a flow diagram and algorithm for a method 72 for registering the TCS and RCS to one another, in accordance with some embodiments of the present invention. For simplicity, FIG. 2 assumes that the registration is performed based on corresponding poses for one particular portion of the ensemble, such as the distal tip of the tool.

Method 72 begins with a first TCS-pose-deriving step 74, at which the processor derives the TCS-pose of the particular portion of the ensemble from sensor-tracking signal 60. Typically, first TCS-pose-deriving step 74 is performed periodically (e.g., once every 5 ms).

To derive the TCS-pose of the particular portion of the ensemble, the processor first derives the TCS-pose of the tool-tracking sensor, using any suitable technique. For example, for an electromagnetic tracking system, the processor may compute the pose of each ensemble-coupled coil from the respective amplitudes of the various components of the sensor-tracking signal. For an optical tracking system, the processor may use computer vision techniques to compute the pose of the optical marker from the images acquired by the cameras. If the particular portion of the ensemble is different from the portion of the ensemble to which the sensor is coupled, the processor then computes the TCS-pose of the particular portion of the ensemble by adding, to the TCS-pose of the sensor, the known pose offset between the particular portion of the ensemble and the sensor.

Subsequently to, or prior to, first TCS-pose-deriving step 74, the processor receives the arm-tracking signal from the robot, at a signal-receiving step 76. For example, the processor may periodically request the arm-tracking signal from the robot immediately subsequently to or prior to first TCS-pose-deriving step 74, such that the robot communicates the arm-tracking signal to the processor. Alternatively, the robot may be configured to periodically (e.g., once every 5 ms) communicate the arm-tracking signal to the processor, even without receiving periodic requests from the processor to communicate the signal.

Subsequently to signal-receiving step 76, the processor derives the RCS-pose of the particular portion of the ensemble from the arm-tracking signal, at an RCS-pose-deriving step 78. First, the processor reads the RCS-pose that is explicitly specified in the arm-tracking signal. If the portion of the arm for which the RCS-pose is specified is different from the particular portion of the ensemble, the processor then adds, to the RCS-pose, the known pose offset between the particular portion of the ensemble and the portion of the arm for which the RCS-pose is specified.

Next, at a checking step 80, the processor checks whether the TCS/RCS registration was already performed. If yes, the processor, based on the TCS/RCS registration, transforms the TCS-pose to the RCS, at a transforming step 82. Subsequently, at a first distance-computing step 84, the processor computes the distance between the transformed pose and the RCS-pose. (For example, the processor may compute a type of SSE between the two poses, as described above in the Overview.) The processor then compares this distance to a predefined threshold, at a first distance-comparing step 86.

(Alternatively, the processor may transform the RCS-pose to the TCS, and then compute the distance between the transformed pose and the TCS-pose.)

If the distance is not less than the threshold—indicating that the base of the robot was likely moved—the processor, at a set-emptying step 88, empties the set of pairs of corresponding poses. Subsequently, the processor, at a set-augmenting step 90, adds the TCS-pose and the RCS-pose to the (empty) set of pairs of corresponding poses. The processor then reregisters the TCS and RCS to one another using the corresponding poses, at a registering step 92. In other words, the processor uses the most recent RCS-pose and TCS-pose, but not any of the previously-acquired RCS-poses and TCS-poses, to reregister the two coordinate systems.

On the other hand, if, at first distance-comparing step 86, the processor ascertains that the distance is not greater than the threshold, the processor performs set-augmenting step 90 without first emptying the set, such that the latest pair of poses is appended to the previously-acquired pairs. The processor then reregisters the TCS and RCS to one another, using the entire set. In other words, the processor uses the most recent RCS-pose and TCS-pose, along with the previously-acquired RCS-poses and TCS-poses contained in the set, to reregister the two coordinate systems.

Returning now to checking step 80, if the processor ascertains that the TCS/RCS registration was not yet performed, the processor immediately performs set-augmenting step 90 (thus initializing the set), followed by registering step 92.

Following registering step 92, the processor returns to first TCS-pose-deriving step 74. Before executing TCS-pose-deriving step 74, the processor may wait for several milliseconds, to achieve the desired periodicity for the acquisition of the poses.

Example Registration Technique

Registering step 92 may be performed using any suitable algorithm such as that described herein. For example, as described above in the Overview, the processor may find the transformation $T_{TCS \rightarrow RCS}$ that minimizes the error function $\Sigma_{i=1}^{i=N}(P_i^{RCS} \ P_i^{RCS}*)$, where each $P_i^{RCS}*$ is the result of applying $T_{TCS-RCS}$ to $P_i^{TCS}$. In some embodiments, this technique is performed as follows:

(i) Define a location matrix $M_L^{TCS}$, which includes, in homogenous form, all of the location vectors, relative to the TCS, in the set of poses, and define an analogous location matrix $M_L^{RCS}$ for the RCS:

$$M_L^{TCS} = \begin{bmatrix} x_1 & \ldots & x_N \\ y_1 & \ldots & y_N \\ z_1 & \ldots & z_N \\ 1 & \ldots & 1 \end{bmatrix}^{TCS}$$

$$M_L^{RCS} = \begin{bmatrix} x_1 & \ldots & x_N \\ y_1 & \ldots & y_N \\ z_1 & \ldots & z_N \\ 1 & \ldots & 1 \end{bmatrix}^{RCS}$$

(ii) Define an orientation matrix $M_O^{TCS}$, which includes, in homogenous form, all of the orientation vectors, relative to the TCS, in the set of poses, and define an analogous orientation matrix $M_O^{RCS}$ for the RCS:

$$M_O^{TCS} = \begin{bmatrix} x'_1 & \ldots & x'_N \\ y'_1 & \ldots & y'_N \\ z'_1 & \ldots & z'_N \\ 1 & \ldots & 1 \end{bmatrix}^{TCS}$$

$$M_O^{RCS} = \begin{bmatrix} x'_1 & \ldots & x'_N \\ y'_1 & \ldots & y'_N \\ z'_1 & \ldots & z'_N \\ 1 & \ldots & 1 \end{bmatrix}^{RCS}$$

(iii) Define a 3×3 rotation matrix $R3(\theta, \phi, \psi)$, which rotates any given 3×1 vector around the x-, y-, and z-axes by the angles $\theta$, $\phi$, and $\psi$, respectively:

$$R3(\theta, \phi, \psi) = \begin{bmatrix} r_{11} & r_{12} & r_{13} \\ r_{21} & r_{22} & r_{23} \\ r_{31} & r_{32} & r_{33} \end{bmatrix}$$

(For simplicity, the dependency of the terms $r_{11} \ldots r_{33}$ on $\theta$, $\phi$, and $\psi$ is not explicitly indicated herein.)

(iv) Define three translations $t_x$, $t_y$, and $t_z$, which translate any given vector along the x-, y-, and z-axes, respectively.

(v) Define a 4×4 rotation matrix R4, which extends R3 to operate on homogenous 4×1 vectors:

$$R4 = \begin{bmatrix} r_{11} & r_{12} & r_{13} & 0 \\ r_{21} & r_{22} & r_{23} & 0 \\ r_{31} & r_{32} & r_{33} & 0 \\ 0 & 0 & 0 & 1 \end{bmatrix}$$

(vi) Define a 4×4 transformation matrix T, which, following the application of the rotation $R3(\theta, \phi, \psi)$ to a vector, translates the vector by the translations $t_x$, $t_y$, and $t_z$:

$$T = \begin{bmatrix} r_{11} & r_{12} & r_{13} & t_x \\ r_{21} & r_{22} & r_{23} & t_y \\ r_{31} & r_{32} & r_{33} & t_z \\ 0 & 0 & 0 & 1 \end{bmatrix}$$

(vii) Let the location matrix $M_L^{RCS}*$ be equal to $T \times M_L^{TCS}$ and the orientation matrix $M_O^{RCS}*$ be equal to $R4 \times M_O^{TCS}$.

(viii) Find $\theta$, $\phi$, $\psi$, $t_x$, $t_y$, and $t_z$ that minimize the distance between $(M_L^{RCS}, M_O^{RCS})$ and $(M_L^{RCS}*, M_O^{RCS}*)$. As noted above in the Overview, this distance may be equal to $\Sigma_{i=1}^{i=N}(x_i^{RCS} - x_i^{RCS}*)^2 + (y_i^{RCS} - y_i^{RCS}*)^2 + (z_i^{RCS} - z_i^{RCS}*)^2 + C(x_i'^{RCS} - x_i'^{RCS}*)^2 + (y_i'^{RCS} - y_i'^{RCS}*)^2 + (z_i'^{RCS} - z_i'^{RCS}*)^2))$ for a suitable constant C.

Controlling the Robot

Figure 3:
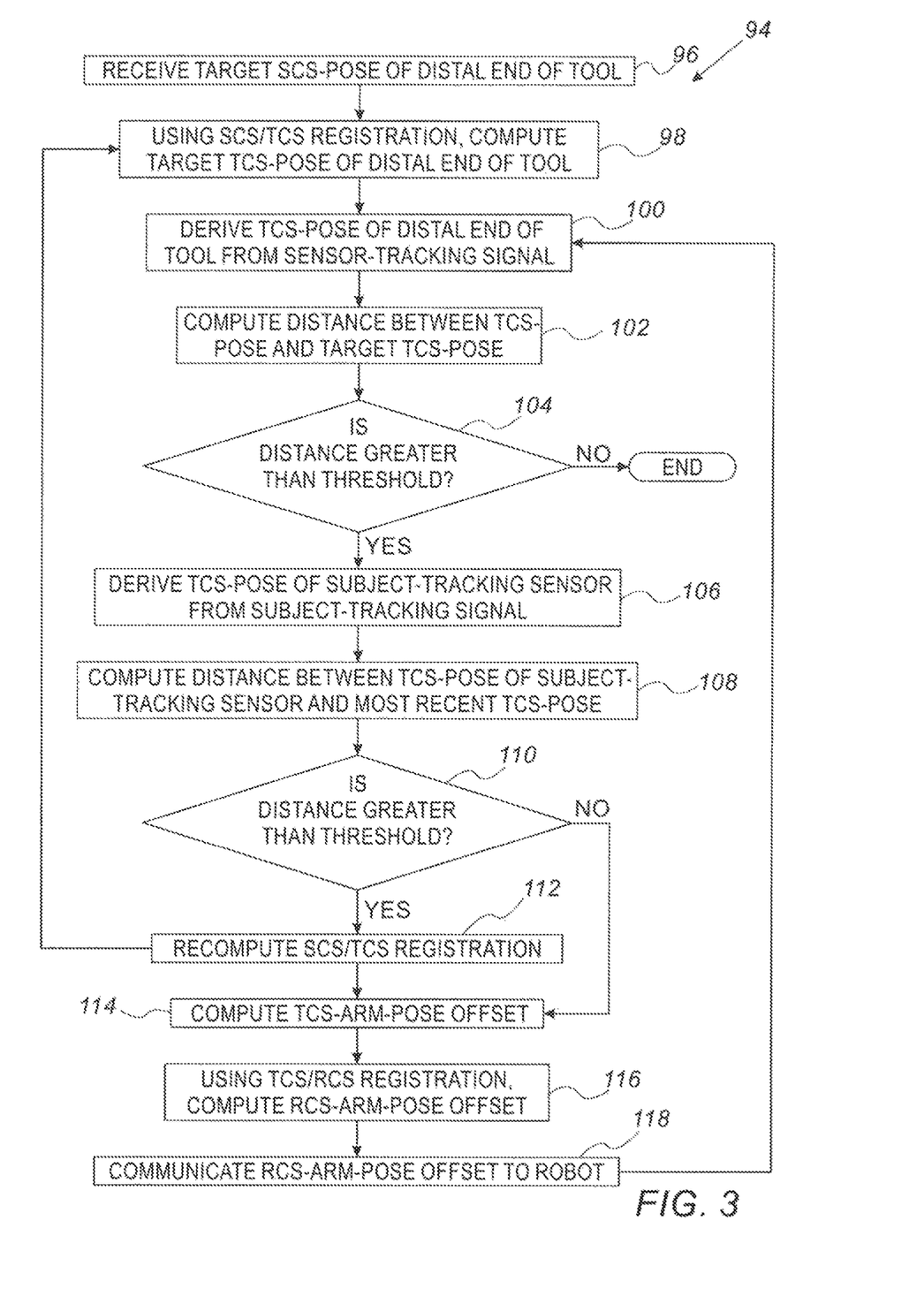
FIG. 3 is a flow diagram for a method and algorithm for controlling a surgical robot, in accordance with some embodiments of the present invention.

Reference is now made to FIG. 3, which is a flow diagram and algorithm for a method 94 for controlling robot 24, in accordance with some embodiments of the present invention. Method 94 is performed by processor 40 in parallel with method 72 (FIG. 2), e.g., by executing the two methods on parallel threads.

Method 94 begins with the receipt, from the physician, of a target pose for the distal end of the tool.

In some embodiments, the target pose is specified in the TCS, e.g., by virtue of the physician manually moving the robotic arm to the target pose. For example, in endoscopic procedures, the robot must typically withdraw the endoscope repeatedly for cleaning, such that it is necessary for the robot to repeatedly return to the target pose that was initially specified by the physician.

In other embodiments, as assumed in FIG. 3, the physician specifies the target pose of the distal end of the tool in the SCS. For example, as described above with reference to FIG. 1, the physician may specify the target pose by drawing or moving an icon that is superimposed over a preoperative scan of the subject. Method 94 thus begins at a target-receiving step 96, at which processor 40 receives a target SCS-pose of the distal end of the tool, i.e., a target pose of the distal end of the tool relative to the SCS. Following target-receiving step 96, the processor, at a target-computing step 98, uses the SCS/TCS registration to compute the target TCS-pose of the distal end of the tool. (As described above in the Overview, the SCS/TCS registration is typically initialized prior to the beginning of the procedure.)

Subsequently, the processor executes a control loop, so as to incrementally move the distal end of the tool toward the target pose. At the beginning of each iteration of the control loop, the processor, at a second TCS-pose-deriving step 100, derives the TCS-pose of the distal end of the tool from the sensor-tracking signal. Subsequently, the processor, at a second distance-computing step 102, computes the distance between the TCS-pose and the target TCS-pose. The processor then compares this distance to a predefined threshold, at a second distance-comparing step 104. If the distance is not greater than the threshold—and thus, the target pose has been attained—the processor exits the control loop, and method 94 ends. Otherwise, the processor moves arm 26 toward the target pose by a small offset, and then returns to the beginning of the control loop. The offset is computed responsively to any changes in the pose of the subject, as computed based on the subject-tracking signal.

(In general, second TCS-pose-deriving step 100 may be performed together with first TCS-pose-deriving step 74 of FIG. 2. For example, the processor may periodically derive the TCS-pose of the sensor, and then derive the TCS-pose of the particular portion of the ensemble and of the distal end of the tool from the TCS-pose of the sensor. Thus, if the particular portion of the ensemble that is used for the TCS/RCS registration is the distal end of the tool, second TCS-pose-deriving step 100 may be identical to first TCS-pose-deriving step 74.)

More specifically, subsequently to ascertaining the distance is greater than the threshold, the processor first derives the TCS-pose of the subject-tracking sensor from the subject-tracking signal, at a third TCS-pose-deriving step 106. Subsequently, at a third distance-computing step 108, the processor computes the distance between the current TCS-pose of the subject-tracking sensor and the most recent TCS-pose. The processor then checks, at a third distance-comparing step 110, whether the distance is greater than a predefined threshold.

If the distance is not less than the threshold—and hence, it may be assumed that the subject has not moved—the processor, at a first offset-computing step 114, computes a target arm-pose offset relative to the TCS. Next, at a second offset-computing step 116, the processor uses the TCS/RCS registration (obtained via method 72 of FIG. 2) to compute a transformed arm-pose offset, referred to in FIG. 3 as an RCS-arm-pose offset; in other words, the processor transforms the TCS-arm-pose offset to the RCS. Subsequently, the processor, at an offset-communicating step 118, causes the robot to change the pose of the arm by the arm-pose offset, by communicating the transformed arm-pose offset to the robot. The processor then returns to second TCS-pose-deriving step 100.

On the other hand, if, at third distance-comparing step 110, the processor ascertains that the distance is greater than the threshold (indicating that the pose of the subject has changed), the processor recomputes the target TCS-pose prior to computing the arm-pose offset. In particular, the processor first recomputes the SCS/TCS registration based on the movement of the subject-tracking sensor, at a registration-recomputing step 112. Subsequently, the processor returns to target-computing step 98, and recomputes the target TCS-pose of the distal end of the tool, using the SCS/TCS registration. (Alternatively, the processor may apply, to the current target TCS-pose, the transformation that maps the most recent TCS-pose of the subject-tracking sensor to the current TCS-pose of the subject-tracking sensor.) The processor then re-executes the control loop, as described above.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A system for controlling a surgical robot while the robot moves an ensemble that includes an arm of the robot and a tool that is held by the arm, the system comprising:
a communication interface; and
a processor, configured to:
receive from the robot via the communication interface, at one or more times, an arm-tracking signal, which indicates an arm-pose of the arm relative to a robot coordinate system (RCS) of the robot,
derive, from the arm-tracking signal, respective RCS-poses of at least one particular portion of the ensemble, relative to the RCS, at the one or more times,
receive, from a tracking system, a sensor-tracking signal, which indicates a sensor-pose of at least one sensor, which belongs to the tracking system and is coupled to the ensemble, relative to a tracking-system coordinate system (TCS) of the tracking system,
derive, from the sensor-tracking signal, respective TCS-poses of the particular portion of the ensemble, relative to the TCS, at the one or more times,
based on the RCS-poses and the TCS-poses, register the RCS and the TCS to one another, and
based on the registering, control the robot, wherein the times are first times, the RCS-poses are first-time RCS-poses, and the TCS-poses are first-time TCS-poses, and wherein the processor is further configured to:
receive the arm-tracking signal at a second time,
derive, from the arm-tracking signal, a second-time RCS-pose of the particular portion of the ensemble, relative to the RCS, at the second time,
derive, from the sensor-tracking signal, a second-time TCS-pose of the particular portion of the ensemble, relative to the TCS, at the second time,
based on the registering, compute a transformed pose, by transforming the second-time TCS-pose to the RCS,
compute a distance between the transformed pose and the second-time RCS-pose, and
responsively to the distance being greater than a predefined threshold, reregister the RCS and the TCS to one another using the second-time RCS-pose and the second-time TCS-pose, without using the first-time RCS-poses and without using the first-time TCS-poses.

2. The system according to claim 1, wherein the sensor includes a coil, and wherein the tracking system includes a plurality of magnetic-field generators that generate a magnetic field that induces the sensor-tracking signal in the coil.

3. The system according to claim 1, wherein the sensor is coupled to the tool.

4. The system according to claim 1, wherein the sensor is coupled to the arm.

5. The system according to claim 1, wherein the processor is configured to control the robot by:
computing a target arm-pose offset relative to the TCS,
based on the registering, computing a transformed target arm-pose offset, by transforming the target arm-pose offset to the RCS, and causing the robot to change the arm-pose of the arm by the target arm-pose offset, by communicating the transformed target arm-pose offset to the robot.

6. The system according to claim 5,
wherein the robot is operating on a subject,
wherein the tracking system further includes at least one subject-tracking sensor coupled to the subject, and
wherein the processor is further configured to:
receive, from the tracking system, a subject-tracking signal, which indicates a subject-tracking-sensor-pose of the subject-tracking sensor relative to the TCS, and
derive, from the subject-tracking signal, a change in a subject-pose of the subject, and
wherein the processor is configured to compute the target arm-pose offset in response to the change in the subject-pose of the subject.

7. A system for controlling a surgical robot while the robot moves an ensemble that includes an arm of the robot and a tool that is held by the arm, the system comprising:
a communication interface; and
a processor, configured to:
receive from the robot via the communication interface, at one or more times, an arm-tracking signal, which indicates an arm-pose of the arm relative to a robot coordinate system (RCS) of the robot,
derive, from the arm-tracking signal, respective RCS-poses of at least one particular portion of the ensemble, relative to the RCS, at the one or more times,
receive, from a tracking system, a sensor-tracking signal, which indicates a sensor-pose of at least one sensor, which belongs to the tracking system and is coupled to the ensemble, relative to a tracking-system coordinate system (TCS) of the tracking system,
derive, from the sensor-tracking signal, respective TCS-poses of the particular portion of the ensemble, relative to the TCS, at the one or more times,
based on the RCS-poses and the TCS-poses, register the RCS and the TCS to one another, and
based on the registering, control the robot, wherein the times are first times, the RCS-poses are first-time RCS-poses, and the TCS-poses are first-time TCS-poses, and wherein the processor is further configured to:
receive the arm-tracking signal at a second time,
derive, from the arm-tracking signal, a second-time RCS-pose of the particular portion of the ensemble, relative to the RCS, at the second time,
derive, from the sensor-tracking signal, a second-time TCS-pose of the particular portion of the ensemble, relative to the TCS, at the second time,
based on the registering, compute a transformed pose, by transforming the second-time TCS-pose to the RCS,
compute a distance between the transformed pose and the second-time RCS-pose, and
responsively to the distance not being greater than a predefined threshold, reregister the RCS and the TCS to one another using the second-time RCS-pose, the second-time TCS-pose, the first-time RCS-poses, and the first-time TCS-poses.

8. The system according to claim 7, wherein the sensor includes a coil, and wherein the tracking system includes a plurality of magnetic-field generators that generate a magnetic field that induces the sensor-tracking signal in the coil.

9. The system according to claim 7, wherein the sensor is coupled to the tool.

10. The system according to claim 7, wherein the sensor is coupled to the arm.

11. The system according to claim 7, wherein the processor is configured to control the robot by:
computing a target arm-pose offset relative to the TCS,
based on the registering, computing a transformed target arm-pose offset, by transforming the target arm-pose offset to the RCS, and
causing the robot to change the arm-pose of the arm by the target arm-pose offset, by communicating the transformed target arm-pose offset to the robot.

12. The system according to claim 11,
wherein the robot is operating on a subject,
wherein the tracking system further includes at least one subject-tracking sensor coupled to the subject, and
wherein the processor is further configured to:
receive, from the tracking system, a subject-tracking signal, which indicates a subject-tracking-sensor-pose of the subject-tracking sensor relative to the TCS, and
derive, from the subject-tracking signal, a change in a subject-pose of the subject, and
wherein the processor is configured to compute the target arm-pose offset in response to the change in the subject-pose of the subject.

13. A system for controlling a surgical robot while the robot moves an ensemble that includes an arm of the robot and a tool that is held by the arm, the system comprising:
a communication interface; and
a processor, configured to:
receive from the robot via the communication interface, at one or more times, an arm-tracking signal, which indicates an arm-pose of the arm relative to a robot coordinate system (RCS) of the robot,
derive, from the arm-tracking signal, respective RCS-poses of at least one particular portion of the ensemble, relative to the RCS, at the one or more times,
receive, from a tracking system, a sensor-tracking signal, which indicates a sensor-pose of at least one sensor, which belongs to the tracking system and is coupled to the ensemble, relative to a tracking-system coordinate system (TCS) of the tracking system,
derive, from the sensor-tracking signal, respective TCS-poses of the particular portion of the ensemble, relative to the TCS, at the one or more times,
based on the RCS-poses and the TCS-poses, register the RCS and the TCS to one another, and
based on the registering, control the robot, wherein the times are first times, the RCS-poses are first-time RCS-poses, and the TCS-poses are first-time TCS-poses, and wherein the processor is further configured to:
receive the arm-tracking signal at a second time,
derive, from the arm-tracking signal, a second-time RCS-pose of the particular portion of the ensemble, relative to the RCS, at the second time,
derive, from the sensor-tracking signal, a second-time TCS-pose of the particular portion of the ensemble, relative to the TCS, at the second time,
based on the registering, compute a transformed pose, by transforming the second-time RCS-pose to the TCS,
compute a distance between the transformed pose and the second-time TCS-pose, and
responsively to the distance being greater than a predefined threshold, reregister the RCS and the TCS to one another using the second-time RCS-pose and the second-time TCS-pose, without using the first-time RCS-poses and without using the first-time TCS-poses.

14. The system according to claim 13, wherein the sensor includes a coil, and wherein the tracking system includes a plurality of magnetic-field generators that generate a magnetic field that induces the sensor-tracking signal in the coil.

15. The system according to claim 13, wherein the sensor is coupled to the tool.

16. The system according to claim 13, wherein the sensor is coupled to the arm.

17. The system according to claim 13, wherein the processor is configured to control the robot by:
computing a target arm-pose offset relative to the TCS,
based on the registering, computing a transformed target arm-pose offset, by transforming the target arm-pose offset to the RCS, and
causing the robot to change the arm-pose of the arm by the target arm-pose offset, by communicating the transformed target arm-pose offset to the robot.

18. The system according to claim 17,
wherein the robot is operating on a subject,
wherein the tracking system further includes at least one subject-tracking sensor coupled to the subject, and
wherein the processor is further configured to:
receive, from the tracking system, a subject-tracking signal, which indicates a subject-tracking-sensor-pose of the subject-tracking sensor relative to the TCS, and
derive, from the subject-tracking signal, a change in a subject-pose of the subject, and
wherein the processor is configured to compute the target arm-pose offset in response to the change in the subject-pose of the subject.

19. A system for controlling a surgical robot while the robot moves an ensemble that includes an arm of the robot and a tool that is held by the arm, the system comprising:
a communication interface; and
a processor, configured to:
receive from the robot via the communication interface, at one or more times, an arm-tracking signal, which indicates an arm-pose of the arm relative to a robot coordinate system (RCS) of the robot,
derive, from the arm-tracking signal, respective RCS-poses of at least one particular portion of the ensemble, relative to the RCS, at the one or more times,
receive, from a tracking system, a sensor-tracking signal, which indicates a sensor-pose of at least one sensor, which belongs to the tracking system and is coupled to the ensemble, relative to a tracking-system coordinate system (TCS) of the tracking system,
derive, from the sensor-tracking signal, respective TCS-poses of the particular portion of the ensemble, relative to the TCS, at the one or more times,
based on the RCS-poses and the TCS-poses, register the RCS and the TCS to one another, and
based on the registering, control the robot, wherein the times are first times, the RCS-poses are first-time RCS-poses, and the TCS-poses are first-time TCS-poses, and wherein the processor is further configured to:
receive the arm-tracking signal at a second time,
derive, from the arm-tracking signal, a second-time RCS-pose of the particular portion of the ensemble, relative to the RCS, at the second time,
derive, from the sensor-tracking signal, a second-time TCS-pose of the particular portion of the ensemble, relative to the TCS, at the second time,
based on the registering, compute a transformed pose, by transforming the second-time RCS-pose to the TCS,
compute a distance between the transformed pose and the second-time TCS-pose, and
responsively to the distance not being greater than a predefined threshold, reregister the RCS and the TCS to one another using the second-time RCS-pose, the second-time TCS-pose, the first-time RCS-poses, and the first-time TCS-poses.

20. The system according to claim 19, wherein the sensor includes a coil, and wherein the tracking system includes a plurality of magnetic-field generators that generate a magnetic field that induces the sensor-tracking signal in the coil.

21. The system according to claim 19, wherein the sensor is coupled to the tool.

22. The system according to claim 19, wherein the sensor is coupled to the arm.

23. The system according to claim 19, wherein the processor is configured to control the robot by:
computing a target arm-pose offset relative to the TCS,
based on the registering, computing a transformed target arm-pose offset, by transforming the target arm-pose offset to the RCS, and
causing the robot to change the arm-pose of the arm by the target arm-pose offset, by communicating the transformed target arm-pose offset to the robot.

24. The system according to claim 23,
wherein the robot is operating on a subject,
wherein the tracking system further includes at least one subject-tracking sensor coupled to the subject, and
wherein the processor is further configured to:
receive, from the tracking system, a subject-tracking signal, which indicates a subject-tracking-sensor-pose of the subject-tracking sensor relative to the TCS, and
derive, from the subject-tracking signal, a change in a subject-pose of the subject, and
wherein the processor is configured to compute the target arm-pose offset in response to the change in the subject-pose of the subject.

25. A method for controlling a surgical robot while the robot moves an ensemble that includes an arm of the robot and a tool that is held by the arm, the method comprising:
receiving from the robot, at one or more times, an arm-tracking signal, which indicates an arm-pose of the arm relative to a robot coordinate system (RCS) of the robot;
deriving, from the arm-tracking signal, respective RCS-poses of at least one particular portion of the ensemble, relative to the RCS, at the one or more times;
receiving, from a tracking system, a sensor-tracking signal, which indicates a sensor-pose of at least one sensor, which belongs to the tracking system and is coupled to the ensemble, relative to a tracking-system coordinate system (TCS) of the tracking system;
deriving, from the sensor-tracking signal, respective TCS-poses of the particular portion of the ensemble, relative to the TCS, at the one or more times;
based on the RCS-poses and the TCS-poses, registering the RCS and the TCS to one another; and
based on the registering, controlling the robot, wherein the times are first times, the RCS-poses are first-time RCS-poses, and the TCS-poses are first-time TCS-poses, and wherein the method further comprises:

receiving the arm-tracking signal at a second time;
deriving, from the arm-tracking signal, a second-time RCS-pose of the particular portion of the ensemble, relative to the RCS, at the second time;
deriving, from the sensor-tracking signal, a second-time TCS-pose of the particular portion of the ensemble, relative to the TCS, at the second time;
based on the registering, computing a transformed pose, by transforming the second-time TCS-pose to the RCS;
computing a distance between the transformed pose and the second-time RCS-pose; and
responsively to the distance being greater than a predefined threshold, reregistering the RCS and the TCS to one another using the second-time RCS-pose and the second-time TCS-pose, without using the first-time RCS-poses and without using the first-time TCS-poses.

26. The method according to claim 25, wherein the sensor includes a coil, and wherein the tracking system includes a plurality of magnetic-field generators that generate a magnetic field that induces the sensor-tracking signal in the coil.

27. The method according to claim 25, wherein the sensor is coupled to the tool.

28. The method according to claim 25, wherein the sensor is coupled to the arm.

29. The method according to claim 25, wherein controlling the robot comprises:
computing a target arm-pose offset relative to the TCS;
based on the registering, computing a transformed target arm-pose offset, by transforming the target arm-pose offset to the RCS; and
causing the robot to change the arm-pose of the arm by the target arm-pose offset, by communicating the transformed target arm-pose offset to the robot.

30. The method according to claim 29,
wherein the robot is operating on a subject,
wherein the tracking system further includes at least one subject-tracking sensor coupled to the subject, and
wherein the method further comprises:
receiving, from the tracking system, a subject-tracking signal, which indicates a subject-tracking-sensor-pose of the subject-tracking sensor relative to the TCS; and
deriving, from the subject-tracking signal, a change in a subject-pose of the subject, and
wherein computing the target arm-pose offset comprises computing the arm-pose offset in response to the change in the subject-pose of the subject.

31. A method for controlling a surgical robot while the robot moves an ensemble that includes an arm of the robot and a tool that is held by the arm, the method comprising:
receiving from the robot, at one or more times, an arm-tracking signal, which indicates an arm-pose of the arm relative to a robot coordinate system (RCS) of the robot;
deriving, from the arm-tracking signal, respective RCS-poses of at least one particular portion of the ensemble, relative to the RCS, at the one or more times;
receiving, from a tracking system, a sensor-tracking signal, which indicates a sensor-pose of at least one sensor, which belongs to the tracking system and is coupled to the ensemble, relative to a tracking-system coordinate system (TCS) of the tracking system;
deriving, from the sensor-tracking signal, respective TCS-poses of the particular portion of the ensemble, relative to the TCS, at the one or more times;
based on the RCS-poses and the TCS-poses, registering the RCS and the TCS to one another; and
based on the registering, controlling the robot, wherein the times are first times, the RCS-poses are first-time RCS-poses, and the TCS-poses are first-time TCS-poses, wherein the times are first times, the RCS-poses are first-time RCS-poses, and the TCS-poses are first-time TCS-poses, and wherein the method further comprises:
receiving the arm-tracking signal at a second time;
deriving, from the arm-tracking signal, a second-time RCS-pose of the particular portion of the ensemble, relative to the RCS, at the second time;
deriving, from the sensor-tracking signal, a second-time TCS-pose of the particular portion of the ensemble, relative to the TCS, at the second time;
based on the registering, computing a transformed pose, by transforming the second-time TCS-pose to the RCS;
computing a distance between the transformed pose and the second-time RCS-pose; and
responsively to the distance not being greater than a predefined threshold, reregistering the RCS and the TCS to one another using the second-time RCS-pose, the second-time TCS-pose, the first-time RCS-poses, and the first-time TCS-poses.

32. The method according to claim 31, wherein the sensor includes a coil, and wherein the tracking system includes a plurality of magnetic-field generators that generate a magnetic field that induces the sensor-tracking signal in the coil.

33. The method according to claim 31, wherein the sensor is coupled to the tool.

34. The method according to claim 31, wherein the sensor is coupled to the arm.

35. The method according to claim 31, wherein controlling the robot comprises:
computing a target arm-pose offset relative to the TCS;
based on the registering, computing a transformed target arm-pose offset, by transforming the target arm-pose offset to the RCS; and
causing the robot to change the arm-pose of the arm by the target arm-pose offset, by communicating the transformed target arm-pose offset to the robot.

36. The method according to claim 35,
wherein the robot is operating on a subject,
wherein the tracking system further includes at least one subject-tracking sensor coupled to the subject, and
wherein the method further comprises:
receiving, from the tracking system, a subject-tracking signal, which indicates a subject-tracking-sensor-pose of the subject-tracking sensor relative to the TCS; and
deriving, from the subject-tracking signal, a change in a subject-pose of the subject, and
wherein computing the target arm-pose offset comprises computing the arm-pose offset in response to the change in the subject-pose of the subject.

37. A method for controlling a surgical robot while the robot moves an ensemble that includes an arm of the robot and a tool that is held by the arm, the method comprising:
receiving from the robot, at one or more times, an arm-tracking signal, which indicates an arm-pose of the arm relative to a robot coordinate system (RCS) of the robot;
deriving, from the arm-tracking signal, respective RCS-poses of at least one particular portion of the ensemble, relative to the RCS, at the one or more times;
receiving, from a tracking system, a sensor-tracking signal, which indicates a sensor-pose of at least one sensor, which belongs to the tracking system and is coupled to the ensemble, relative to a tracking-system coordinate system (TCS) of the tracking system;

deriving, from the sensor-tracking signal, respective TCS-poses of the particular portion of the ensemble, relative to the TCS, at the one or more times;

based on the RCS-poses and the TCS-poses, registering the RCS and the TCS to one another; and based on the registering, controlling the robot, wherein the times are first times, the RCS-poses are first-time RCS-poses, and the TCS-poses are first-time TCS-poses, wherein the times are first times, the RCS-poses are first-time RCS-poses, and the TCS-poses are first-time TCS-poses, and wherein the method further comprises:

receiving the arm-tracking signal at a second time;

deriving, from the arm-tracking signal, a second-time RCS-pose of the particular portion of the ensemble, relative to the RCS, at the second time;

deriving, from the sensor-tracking signal, a second-time TCS-pose of the particular portion of the ensemble, relative to the TCS, at the second time;

based on the registering, computing a transformed pose, by transforming the second-time RCS-pose to the TCS;

computing a distance between the transformed pose and the second-time TCS-pose; and responsively to the distance being greater than a predefined threshold, reregistering the RCS and the TCS to one another using the second-time RCS-pose and the second-time TCS-pose, without using the first-time RCS-poses and without using the first-time TCS-poses.

38. The method according to claim 37, wherein the sensor includes a coil, and wherein the tracking system includes a plurality of magnetic-field generators that generate a magnetic field that induces the sensor-tracking signal in the coil.

39. The method according to claim 37, wherein the sensor is coupled to the tool.

40. The method according to claim 37, wherein the sensor is coupled to the arm.

41. The method according to claim 37, wherein controlling the robot comprises:

computing a target arm-pose offset relative to the TCS;

based on the registering, computing a transformed target arm-pose offset, by transforming the target arm-pose offset to the RCS; and causing the robot to change the arm-pose of the arm by the target arm-pose offset, by communicating the transformed target arm-pose offset to the robot.

42. The method according to claim 41, wherein the robot is operating on a subject, wherein the tracking system further includes at least one subject-tracking sensor coupled to the subject, and wherein the method further comprises:

receiving, from the tracking system, a subject-tracking signal, which indicates a subject-tracking-sensor-pose of the subject-tracking sensor relative to the TCS; and deriving, from the subject-tracking signal, a change in a subject-pose of the subject, and wherein computing the target arm-pose offset comprises computing the arm-pose offset in response to the change in the subject-pose of the subject.

43. A method for controlling a surgical robot while the robot moves an ensemble that includes an arm of the robot and a tool that is held by the arm, the method comprising:

receiving from the robot, at one or more times, an arm-tracking signal, which indicates an arm-pose of the arm relative to a robot coordinate system (RCS) of the robot;

deriving, from the arm-tracking signal, respective RCS-poses of at least one particular portion of the ensemble, relative to the RCS, at the one or more times;

receiving, from a tracking system, a sensor-tracking signal, which indicates a sensor-pose of at least one sensor, which belongs to the tracking system and is coupled to the ensemble, relative to a tracking-system coordinate system (TCS) of the tracking system;

deriving, from the sensor-tracking signal, respective TCS-poses of the particular portion of the ensemble, relative to the TCS, at the one or more times;

based on the RCS-poses and the TCS-poses, registering the RCS and the TCS to one another; and based on the registering, controlling the robot, wherein the times are first times, the RCS-poses are first-time RCS-poses, and the TCS-poses are first-time TCS-poses, wherein the times are first times, the RCS-poses are first-time RCS-poses, and the TCS-poses are first-time TCS-poses, and wherein the method further comprises:

receiving the arm-tracking signal at a second time;

deriving, from the arm-tracking signal, a second-time RCS-pose of the particular portion of the ensemble, relative to the RCS, at the second time;

deriving, from the sensor-tracking signal, a second-time TCS-pose of the particular portion of the ensemble, relative to the TCS, at the second time;

based on the registering, computing a transformed pose, by transforming the second-time RCS-pose to the TCS;

computing a distance between the transformed pose and the second-time TCS-pose; and responsively to the distance not being greater than a predefined threshold, reregistering the RCS and the TCS to one another using the second-time RCS-pose, the second-time TCS-pose, the first-time RCS-poses, and the first-time TCS-poses.

44. The method according to claim 43, wherein the sensor includes a coil, and wherein the tracking system includes a plurality of magnetic-field generators that generate a magnetic field that induces the sensor-tracking signal in the coil.

45. The method according to claim 43, wherein the sensor is coupled to the tool.

46. The method according to claim 43, wherein the sensor is coupled to the arm.

47. The method according to claim 43, wherein controlling the robot comprises:

computing a target arm-pose offset relative to the TCS;

based on the registering, computing a transformed target arm-pose offset, by transforming the target arm-pose offset to the RCS; and causing the robot to change the arm-pose of the arm by the target arm-pose offset, by communicating the transformed target arm-pose offset to the robot.

48. The method according to claim 47, wherein the robot is operating on a subject, wherein the tracking system further includes at least one subject-tracking sensor coupled to the subject, and wherein the method further comprises:

receiving, from the tracking system, a subject-tracking signal, which indicates a subject-tracking-sensor-pose of the subject-tracking sensor relative to the TCS; and deriving, from the subject-tracking signal, a change in a subject-pose of the subject, and wherein computing the target arm-pose offset comprises computing the arm-pose offset in response to the change in the subject-pose of the subject.

* * * * *